US009469877B2

(12) United States Patent
Sokolova et al.

(10) Patent No.: US 9,469,877 B2
(45) Date of Patent: Oct. 18, 2016

(54) MATERIALS AND METHODS FOR DIAGNOSIS, PROGNOSIS, MONITORING OF RECURRENCE, AND ASSESSMENT OF THERAPEUTIC/PROPHYLACTIC TREATMENT OF PANCREATOBILIARY CANCER

(71) Applicants: ABBOTT MOLECULAR INC., Des Plaines, IL (US); MAYO FOUNDATION FOR MEDICAL EDUCATION AND RESEARCH, Rochester, MN (US)

(72) Inventors: Irina Sokolova, Villa Park, IL (US); Larry Morrison, Oro Valley, AZ (US); Ekaterina Pestova, Glenview, IL (US); Emily Barr Fritcher, Rochester, MN (US); Lewis Roberts, Rochester, MN (US); Gregory Gores, Rochester, MN (US); Kevin Halling, Rochester, MN (US); Benjamin Kipp, Rochester, MN (US)

(73) Assignees: Abbott Molecular Inc., Des Plaines, IL (US); Mayo Foundation For Medical Education and Research, Rochester, MN (US)

( * ) Notice: Subject to any disclaimer, the term of this patent is extended or adjusted under 35 U.S.C. 154(b) by 19 days.

(21) Appl. No.: 13/721,085

(22) Filed: Dec. 20, 2012

(65) Prior Publication Data

US 2013/0171639 A1 Jul. 4, 2013

Related U.S. Application Data

(60) Provisional application No. 61/581,810, filed on Dec. 30, 2011.

(51) Int. Cl.
*C12Q 1/68* (2006.01)
*C07H 21/02* (2006.01)
*C07H 21/04* (2006.01)

(52) U.S. Cl.
CPC ........... *C12Q 1/6886* (2013.01); *C12Q 1/6827* (2013.01); *C12Q 2600/112* (2013.01)

(58) Field of Classification Search
None
See application file for complete search history.

(56) References Cited

U.S. PATENT DOCUMENTS

| 5,491,224 | A | 2/1996 | Bittner et al. |
| 5,756,696 | A | 5/1998 | Gray et al. |
| 6,582,908 | B2* | 6/2003 | Fodor et al. ............... 506/9 |
| 2003/0087248 | A1* | 5/2003 | Morrison ............ C12Q 1/6841 435/6.16 |
| 2005/0252773 | A1 | 11/2005 | McBride et al. |
| 2009/0069194 | A1 | 3/2009 | Ramakrishnan |

FOREIGN PATENT DOCUMENTS

| WO | 9318186 A1 | 9/1993 |
| WO | 9617958 A1 | 6/1996 |

OTHER PUBLICATIONS

NEB catalog (1998/1999), pp. 121, 284.*
Ahern (The Scientist, vol. 9, 1995, from the internet, pp. 1-5).*
Lewin et al; The International Journal of Biochemistry and Cell biology, vol. 39, 2007, pp. 1539-1550.*
Andy Choo K.H., ed., In Situ Hibridization Protocols: Methods in Molecular Biology, vol. 33, Humana Press Inc., 1994, Table of Contents.
Birnbaum D.J., et al., "Genome Profiling of Pancreatic Adenocarcinoma," Genes, Chromosomes and Cancer, 2011, vol. 50 (6), pp. 456-465.
Caldas C., et al., "Frequent Somatic Mutations and Homozygous Deletions of the p16 (MTS1) Gene in Pancreatic Adenocarcinoma," Nature Genetics, 1994, vol. 8 (1), pp. 27-32.
Carter N.P., "Methods and Strategies for Analyzing Copy Number Variation Using DNA Microarrays," Nature Genetics, 2007, vol. 39 (Suppl. 7), pp. S16-S21.
Dehaan R.D., et al., "An Assessment of Chromosomal Alterations Detected by Fluorescence in situ Hybridization and p16 Expression in Sporadic and Primary Sclerosing Cholangitis-Associated Cholangiocarcinomas," Human Pathology, 2007, vol. 38 (3), pp. 491-499.
Delpu Y., et al., "Genetic and Epigenetic Alterations in Pancreatic Carcinogenesis," Current Genomics, 2011, vol. 12 (1), pp. 15-24.
Fritcher E.G., et al., "A Multivariable Model Using Advanced Cytologic Methods for the Evaluation of Indeterminate Pancreatobiliary Strictures," Gastroenterology, 2009, vol. 136 (7), pp. 2180-2186.

(Continued)

*Primary Examiner* — Jehanne Sitton
(74) *Attorney, Agent, or Firm* — Lisa V. Mueller; Michael Best & Friedrich LLP

(57) ABSTRACT

A method of detecting high-grade dysplasia, pancreatobiliary cancer, or metastatic cancer to the pancreatobiliary tract or inferring an increased risk thereof, comprising obtaining a sample of pancreatobiliary cells from a patient with a set of detectably labeled probes comprising a locus-specific probe for MCL1 (myeloid cell leukemia sequence 1), a locus-specific probe for EGFR (epidermal growth factor receptor), a locus-specific probe for MYC, and a locus-specific probe for P16 under hybridization conditions and determining the presence of chromosomal abnormalities; a set of probes comprising a locus-specific probe for MCL1, a locus-specific probe for EGFR, a locus-specific probe for MYC, and a locus-specific probe for P16; and a kit comprising the set of probes and instructions for detecting high-grade dysplasia, pancreatobiliary cancer, or metastatic cancer to the pancreatobiliary tract, or inferring an increased risk thereof, in a patient.

3 Claims, 2 Drawing Sheets

(56) References Cited

OTHER PUBLICATIONS

Gonda T.A, et al., "Polysomy and p16 Deletion by Fluorescence in Situ Hybridization in the Diagnosis of Indeterminate Biliary Strictures," Gastrointestinal Endoscopy, 2011, vol. 75 (1), pp. 74-79.
Gwak G.Y., et al., "Detection of Response-Predicting Mutations in the Kinase Domain of the Epidermal Growth Factor Receptor Gene in Cholangiocarcinomas," Journal of Cancer Research and Clinical Oncology, 2005, vol. 131 (10), pp. 649-652.
Halling K.C., et al., "Fluorescence In Situ Hybridization in Diagnostic Cytology," Human Pathology, 2007, vol. 38, pp. 1137-1144.
Harder J., et al., "EGFR and HER2 Expression in Advanced Biliary Tract Cancer," World Journal of Gastroenterology, 2009, vol. 15 (36), pp. 4511-4517.
Herrick J., et al., "Quantifying Single Gene Copy Number by Measuring Fluorescent Probe Lengths on Combed Genomic DNA," Proceedings of the National Academy of Sciences, 2000, vol. 97 (1), pp. 222-227.
Huo Z., et al., "Intraductal Papillary Mucinous Neoplasm of Pancreas: A Clinicopathologic and Immunohistochemical Study of 19 Cases," Chinese Journal of Pathology, 2008, vol. 37 (10), pp. 670-675.
International Search Report for Application No. PCT/US2012/070747, mailed on May 14, 2013, 3 pages.
Ito Y., et al., "Expression and Clinical Significance of the erbB Family in Intrahepatic Cholangiocellular Carcinoma," Pathology, Practice and Research, 2001, vol. 197 (2), pp. 95-100.
Kallioniemi A., et al., "Comparative Genomic Hybridization for Molecular Cytogenetic Analysis of Solid Tumors," Science, 1992, vol. 258 (5083), pp. 818-821.
Kallioniemi O.P., et al., "ERBB2 Amplification in Breast Cancer Analyzed by Fluorescence in Situ Hybridization," Proceedings of the National Academy of Sciences, 1992, vol. 89 (12), pp. 5321-5325.
Karamitopoulou E., et al., "Clinical Significance of Cell Cycle- and Apoptosis-Related Markers in Biliary Tract Cancer: A Tissue Microarray-Based Approach Revealing a Distinctive Immunophenotype for Intrahepatic and Extrahepatic Cholangiocarcinomas," American Journal of Clinical Pathology, 2008, vol. 130 (5), pp. 780-786.
Kumar J., et al., "Detection of Differential Gene Copy Number Using Denaturing High Performance Liquid Chromatography," Journal of Biochemical and Biophysical Methods, 2005, vol. 64 (3), pp. 226-234.
Lee J.Y., et al., "Genetic Alterations in Intrahepatic Cholangiocarcinoma as Revealed by Degenerate Oligonucleotide Primed PCR-Comparative Genomic Hybridization," Journal of Korean Medical Science, 2004, vol. 19 (5), pp. 682-687.
Liu Z., at al., "Simple Copy Number Determination with Reference Query Pyrosequencing (RQPS)," Cold Spring Harbor Protocols, 2010, vol. 2010 (9), 10 pages.
McKay S.C., et al., "Array Comparative Genomic Hybridization Identifies Novel Potential Therapeutic Targets in Cholangiocarcinoma," HPB—International Hepato-Pancreato-Biliary Association, 2011, vol. 13 (5), pp. 309-319.
Miller G., et al., "Genome Wide Analysis and Clinical Correlation of Chromosomal and Transcriptional Mutations in Cancers of the Biliary Tract," Journal of Experimental and Clinical Cancer Research, 2009, vol. 28, pp. 62.
Miyamoto Y., et al., "Immunohistochemical Analysis of Bcl-2, Bax, Bcl-X, and Mcl-1 Expression in Pancreatic Cancers," Oncology, 1999, vol. 56 (1), pp. 73-82.
Moreno Luna L.E., et al., "Advanced Cytologic Techniques for the Detection of Malignant Pancreatobiliary Strictures," Gastroenterology, 2006, vol. 131 (4), pp. 1064-1072.
Morrison, L.E. et al., "Labeling Fluorescence In Situ Hybridization Probes for Genomic Targets," Methods in Molecular Biology, 2002, vol. 204, pp. 21-40.
Pinkel D., et al., "Fluorescence in Situ Hybridization with Human Chromosome-Specific Libraries: Detection of Trisomy 21 and Translocations of Chromosome 4," Proceedings of the National Academy of Sciences, 1988, vol. 85 (23), pp. 9138-9142.
Rigby P.W., et al., "Labeling Deoxyribonucleic Acid to High Specific Activity in Vitro by Nick Translation with DNA Polymerase I," Journal of Molecular Biology, 1977, vol. 113 (1), pp. 113-237.
Saito S., et al., "The Genetic Differences Between Gallbladder and Bile Duct Cancer Cell Lines," Oncology Reports, 2006, vol. 16 (5), pp. 949-956.
Sambrook J., et al., eds., Molecular Cloning: A Laboratory Manual, 3rd Edition, Cold Spring Harbor Laboratory, 2001, Table of Contents.
Schouten J.P., et al. , "Relative Quantification of 40 Nucleic Acid Sequences by Multiplex Ligation-dependent Probe Amplification," Nucleic Acids Research, 2002, vol. 30 (12), pp. e57.
Service R.F., , "Gene Sequencing. The Race for the $1000 Genome," Science, 2006, vol. 311 (5767), pp. 1544-1546.
Shendure J., et al., "Advanced Sequencing Technologies: Methods and Goals," Nature Reviews. Genetics, 2004, vol. 5 (5), pp. 335-344.
Shiraishi K., et al., "A Comparison of DNA Copy Number Changes Detected by Comparative Genomic Hybridization in Malignancies of the Liver, Biliary Tract and Pancreas," Oncology, 2001, vol. 60 (2), pp. 151-161.
Thosani N., et al., "Molecular Pathogenesis of Intraductal Papillary Mucinous Neoplasms of the Pancreas," Pancreas, 2010, vol. 39 (8), pp. 1129-1133.
Tijssen P., "Hybridization with Nucleic Acid Probes" in: Laboratory Techniques in Biochemistry and Molecular Biology, vol. 24, Chapter 2, Van der Vliet P.C., ed., Elsevier Publisher, 1993, pp. 19-78.
Tonini G., et al., "Molecular Prognostic Factors in Patients with Pancreatic Cancer," Expert Opinion on Therapeutic Targets, 2007, vol. 11 (12), pp. 1553-1569.
Vogelstein B., et al., "Digital PCR," Proceedings of the National Academy of Sciences, 1999, vol. 96 (16), pp. 9236-9241.
Werneburg N.W., et al., "Tumor Necrosis Factor-Related Apoptosis-Inducing Ligand Activates a Lysosomal Pathway of Apoptosis that is Regulated by Bcl-2 Proteins," Journal of Biological Chemistry, 2007, vol. 282 (39), pp. 28960-28970.
Yang Z.M., et al., "Analysis of Chromosomal Abnormalities in Pancreatic Cancer by Spectral Karyotyping," Chinese Journal of Pathology, 2010, vol. 39 (11), pp. 767-771.
Yoshikawa D., et al., "Clinicopathological and Prognostic Significance of EGFR, VEGF and HER2 Expression in Cholangiocarcinoma," British Journal of Cancer, 2008, vol. 98 (2), pp. 418-425.
Written Opinion for Application No. PCT/US2012/070747 dated Jun. 30, 2014 (8 pages).

* cited by examiner

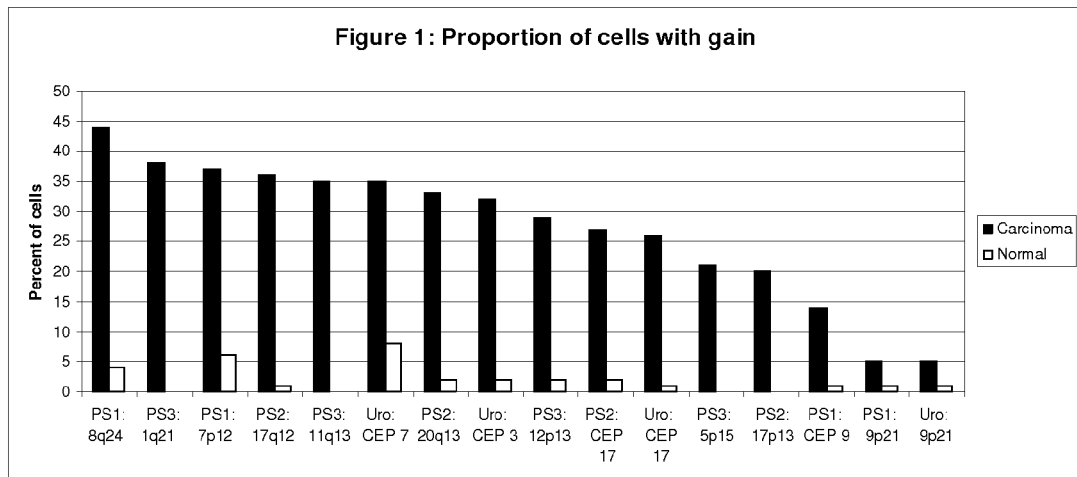
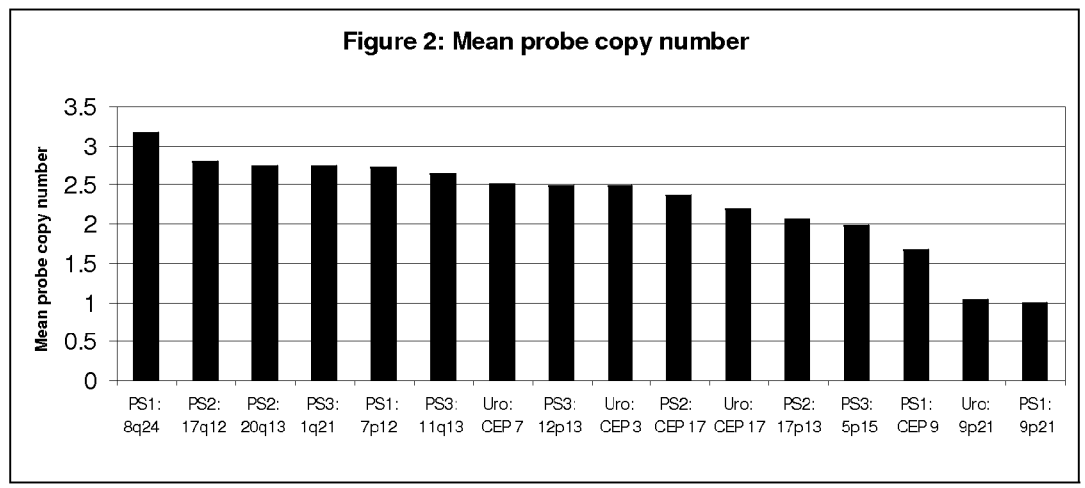

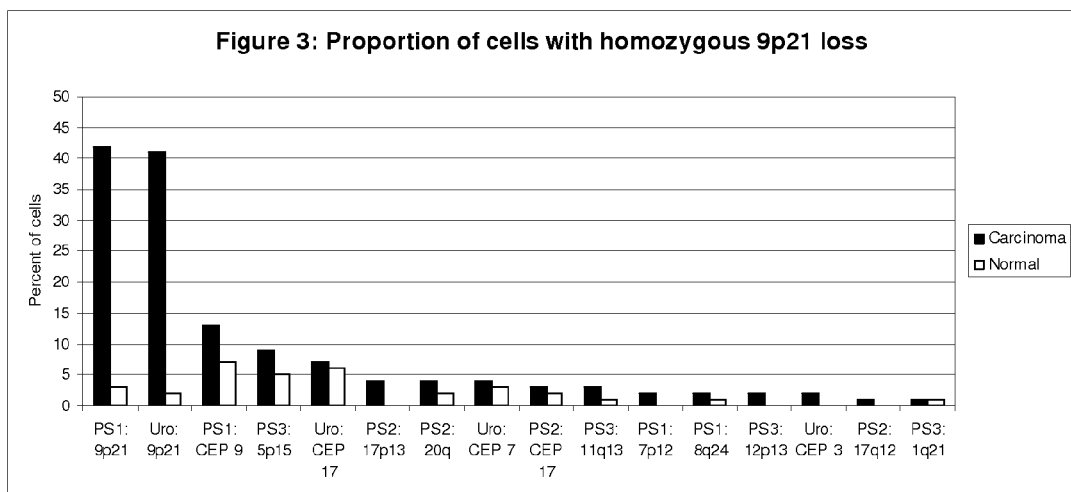

MATERIALS AND METHODS FOR DIAGNOSIS, PROGNOSIS, MONITORING OF RECURRENCE, AND ASSESSMENT OF THERAPEUTIC/PROPHYLACTIC TREATMENT OF PANCREATOBILIARY CANCER

CROSS REFERENCE TO RELATED APPLICATIONS

This application claims priority to U.S. provisional patent application No. 61/581,810, which was filed on Dec. 30, 2011, and the content of which is hereby incorporated by reference in its entirety.

TECHNICAL FIELD

The present disclosure relates to methods of diagnosis, prognosis, monitoring of recurrence, and assessment of the therapeutic or prophylactic treatment of cancer, in particular pancreatobiliary cancer, the detection of genotypic abnormalities, and in situ hybridization, as well as a set of probes and a kit useful in such methods.

BACKGROUND

Cholangiocarcinoma (CCA), a malignancy arising from bile duct epithelium, and pancreatic carcinoma are the most common tumor types found in the pancreatobiliary tract. High mortality is associated with these cancers with a five-year survival rate of less than 5%. Pancreatic carcinoma was the tenth most common type of cancer in the United States in 2009 but was the fourth most common cause of cancer death among Americans.

While CCA is a relatively rare tumor, its incidence is increasing worldwide for reasons that are unclear. Evidence suggests that chronic inflammation predisposes biliary epithelium to the development of carcinoma. Therefore, patients with primary sclerosing cholangitis (PSC) are at increased risk of cholangiocarcinoma. PSC patients typically receive regular ERCP surveillance including cytologic brushing of suspicious areas.

Patients with pancreatobiliary malignancy tend to present with symptoms at late stage when chance of successful intervention is low. Early detection offers patients their best chance for surgical resection, which is currently the most viable treatment option.

Acquisition of adequate and diagnostic tissue during endoscopic retrograde cholangiopancreatography (ERCP) is challenging. Successful biopsy collection can be hampered by challenging anatomical location of some structures. Pancreatobiliary biopsies tend to be small, inadequate, and/or lacking diagnostic cells. Pathological evidence of tumor (e.g., biopsy, cytological brushing, and fine needle aspiration (FNA)) is necessary to confirm a suspicion of carcinoma; however, current diagnostic assays have limited sensitivity for detection of malignancy. Cytologic brushings can be performed during ERCP and, because they can sample the entire area under scrutiny for carcinoma, may provide a diagnosis of malignancy when histology is negative, but the sensitivity of routine cytology is suboptimal. The detection rate for carcinoma by routine cytological analysis of ERCP brushings is relatively low (20% at the Mayo Clinic). Use of digital image analysis (DIA) and fluorescence in situ hybridization (FISH) on cytological brushings have improved detection rates for carcinoma over routine cytology; however, DIA has been shown to not be an independent predictor of malignancy and has been discontinued (Fritcher et al., Gastroeneterology 136(7): 2180-2186 (2009)). FISH utilizing probes originally designed for the detection of bladder cancer (UroVysion™, Abbott Molecular, Des Plaines, Ill.) has been shown to be an independent predictor of malignancy (Fritcher et al. (2009), supra). However, while FISH detects approximately twice as many cases of carcinoma compared to routine cytology, it fails to detect half of the cancer specimens. UroVysion™ contains a locus-specific probe directed to the P16 gene, which is a tumor-suppressor gene located on the short arm of chromosome 9 and is known to be deleted in a proportion of pancreatobiliary carcinomas (Caldas et al., Nature Genetics 8(1): 27-32 (1994); see, also, erratum in Nature Genetics 8(4): 410 (1994)); however, a threshold for positivity has not been established and, therefore, to Applicants' knowledge, this probe is not being evaluated in current clinical practice. Imaging modalities, such as computed tomography, ultrasound, and magnetic resonance imaging (MRI), allow for visualization of the pancreatobiliary tract. Differentiation between benign and malignant structures using imaging is not always possible, however. Serum tumor marker levels, such as CA19-9, can be elevated in patients with pancreatobiliary malignancy, but such markers are not specific for carcinoma and, hence, have limited utility.

Miyamoto et al. (Oncology 56(1): 73-82 (1999)) reportedly investigated the expression of several members of the Bcl-2 family proteins in pancreatic cancer using immunohistochemical analysis of 30 invasive ductal adenocarcinomas and 23 intraductal papillary-mucinous tumors (IPMTs) and immunoblot analysis of six cancer tissues and seven pancreatic cancer cell lines. Mcl-1 (myeloid cell leukemia sequence 1) expression was reportedly found in 90% of the invasive ductal adenocarcinomas and 88% of intraductal papillary-mucinous adenocarcinomas. Mcl-1 protein levels were reportedly uniformly high in all pancreatic cancer cell lines.

McKay et al. (HPB (Oxford) 13(5): 309-319 (May 2011; epub Mar. 10, 2011)) reportedly used array comparative genomic hybridization to identify novel potential therapeutic targets in CCA. Regions covering the EGFR (epidermal growth factor receptor) gene, among others, were reportedly frequently gained. Harder et al. (World J. Gastroenterol. 15(36): 4511-4517 (Sep. 28 2009)) have reported that EGFR may be a promising therapeutic target in patients with advanced biliary tract cancer. Yoshikawa et al. (Br. J. Cancer 98(2): 418-425 (Jan. 29, 2008; epub Dec. 18, 2007)) reportedly assessed 236 cases of CCA retrospectively using immunohistochemical analysis of EGFR, among other genes. They reportedly observed an association between overexpression of EGFR with macroscopic type, lymph node metastasis, tumor stage, lymphatic vessel invasion, and perineural invasion in extrahepatic cholangiocarcinoma (EHCC). EGFR expression was reportedly found to be a significant prognostic factor and a risk factor for tumor recurrence. Based on such results, they suggested that EGFR expression is associated with tumor expression in CCA (see, also, Ito et al., Pathol. Res. Pract. 197(2): 95-100 (2001)). Gwak et al. (J. Cancer Res. Clin. Oncol. 131(10): 649-652 (October 2005; epub Oct. 20, 2005)) reportedly observed deletions in exon 19 of the EGFR gene were more commonly found in intra-hepatic or poorly differentiated CCAs.

A gain/amplification of the MYC gene, among others, in pancreatic adenocarcinoma has been reported by Birnbaum et al. (Genes Chromosomes Cancer 50(6): 456-465 (June 2011; epub Mar. 15, 2011)).

Alteration of the P16 gene, among other genes, reportedly is frequently observed in pancreatic ductal adenocarcinoma (PDAC) (Delpu et al., Curr. Genomics 12(1): 15-24 (March 2011)) and intraductal papillary mucinous neoplasm (IPMN) (Huo et al., Zhonghua Bing Li Xue Za Zhi 37(10): 670-675 (October 2008)). Karamitopoulou et al. also disclose that P16 reportedly is an important prognostic marker in CCA (Am. J. Clin. Pathol. 130(5): 780-786 (November 2008)). Tonini et al. disclose that there reportedly is strong evidence for P16, among others, as an independent predictor of patient outcome for pancreatic cancer (Expert Opin. Ther. Targets 11(12): 1553-1569 (December 2007)). Such changes reportedly arise gradually during carcinogenesis. Frequent somatic mutations and homozygous deletion of the P16 (MTS1) gene have been reported in pancreatic adenocarcinoma (Caldas et al. (1994), supra). Others report that such changes can be used to differentiate between cancer and chronic inflammation (see, e.g., Thosani et al., Pancreas 39(8): 1129-1133 (November 2010)).

In view of the foregoing, there remains a need for more sensitive, more reliable, and more informative diagnostic and prognostic methods in the management of pancreatobiliary cancer. The present disclosure seeks to provide a set of markers, as well as methods of use and a kit comprising the set of markers, for the diagnosis, prognosis, and the assessment of the therapeutic or prophylactic treatment of pancreatobiliary cancer. Extensive testing of various markers, as described herein, was necessary to determine the best combination of markers for optimal detection of pancreatobiliary cancer. This and other objects and advantages, as well as inventive features, will become apparent from the detailed description provided herein.

SUMMARY

A method of detecting high-grade dysplasia, pancreatobiliary cancer, metastatic cancer to the pancreatobiliary tract, or inferring an increased risk thereof, in a patient is provided. The method comprises contacting a sample of pancreatobiliary cells, such as a brushing specimen collected during endoscopic retrograde cholangiopancreatography (ERCP), from the patient with a set of detectably labeled probes comprising a locus-specific probe for myeloid cell leukemia sequence 1 (MCL1), a locus-specific probe for epidermal growth factor receptor (EGFR), a locus-specific probe for MYC, and a locus-specific probe for P16, under hybridization conditions and determining the presence of chromosomal abnormalities. Polysomy is indicative of high-grade dysplasia, pancreatobiliary cancer, or metastatic cancer to the pancreatobiliary tract, whereas tetrasomy, a loss of P16, a single locus gain of MCL1, MYC or P16, or a single locus gain of MCL1, EGFR or MYC with concurrent P16 loss infers increased risk of high-grade dysplasia, pancreatobiliary cancer, or metastatic cancer to the pancreatobiliary tract.

A set of probes is also provided. The set of probes comprises a locus-specific probe for MCL1, a locus-specific probe for EGFR, a locus-specific probe for MYC, and a locus-specific probe for P16.

A kit is also provided. The kit comprises (a) a set of probes that enables detection of pancreatobiliary cancer in a patient, wherein the set of probes comprises a locus-specific probe for MCL1, a locus-specific probe for EGFR, a locus-specific probe for MYC, and a locus-specific probe for P16 and (b) instructions for detecting pancreatobiliary cancer in a patient, wherein the instructions comprise determining in a sample of pancreatobiliary cells obtained from the patient the presence of chromosomal abnormalities. Polysomy is indicative of high-grade dysplasia, pancreatobiliary cancer, or metastatic cancer to the pancreatobiliary tract, whereas tetrasomy, P16 loss, a single locus gain of MCL1, MYC or P16, or a single locus gain of MCL1, EGFR, or MYC with concurrent P16 loss infers increased risk of high-grade dysplasia, pancreatobiliary cancer, or metastatic cancer to the pancreatobiliary tract.

BRIEF DESCRIPTION OF THE FIGURES

FIG. 1 is a bar graph of percent of cells vs. probe, wherein the clear bars represent normal and the shaded bars represent carcinomas.

FIG. 2 is a bar graph of mean probe copy number vs. probe.

FIG. 3 is a bar graph of percent of cells with homozygous loss vs. probe.

DETAILED DESCRIPTION

The present disclosure provides a set of markers, as well as a method of use and a kit comprising the set of markers, for the diagnosis, the prognosis, the monitoring of the recurrence, and the assessment of the therapeutic or prophylactic treatment of pancreatobiliary cancer. The following terms are relevant to the present disclosure:

"About" refers to approximately a +/−10% variation from the stated value. It is to be understood that such a variation is always included in any given value provided herein, whether or not specific reference is made to it.

"Biomarker," as defined by the National Institutes of Health, is "a characteristic that is objectively measured and evaluated as an indicator of normal biologic processes, pathogenic processes, or pharmacologic responses to a therapeutic intervention."

"Cholangiocarcinoma (CCA)" is cancer of the bile ducts, which drain bile from the liver. It is a relatively rare adenocarcinoma or glandular cancer that is considered to be incurable and rapidly lethal unless all of the tumor(s) can be fully resected.

"Chromosome enumeration probe (CEP)" or "centromeric probe" is any probe that enables the number of specific chromosomes in a cell to be enumerated. A chromosome enumeration probe typically recognizes and binds to a region near to (referred to as "peri-centromeric") or at the centromere of a specific chromosome, typically a repetitive DNA sequence (e.g., alpha satellite DNA). The centromere of a chromosome is typically considered to represent that chromosome, since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals corresponding to the centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes, since the loss of signals for such probes may not always indicate a loss of the entire chromosome. Examples of chromosome enumeration probes include CEP® probes commercially available from Abbott Molecular, Inc., Des Plaines, Ill. (formerly Vysis, Inc., Downers Grove, Ill.).

"Copy number" is a measurement of DNA, whether of a single locus, one or more loci, or an entire genome. A "copy number" of two is "wild-type" in a human (because of diploidy, except for sex chromosomes). A "copy number" of other than two in a human (except for sex chromosomes) deviates from wild-type. Such deviations include amplifications, i.e., increases in copy numbers, and deletions, i.e., decreases in copy numbers and even the absence of copy numbers.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling. The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Locus-specific probe" and "locus-specific identifier (LSI)" may be used interchangeably herein to refer to a probe that selectively binds to a specific locus in a region on a chromosome, e.g., a locus that has been determined to undergo gain/loss in metastasis. A probe can target coding or non-coding regions, or both, including exons, introns, and/or regulatory sequences, such as promoter sequences and the like.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Pancreatobiliary cancer" includes all types of pancreatobiliary cancer, such as all types of pancreatic carcinoma, e.g., pancreatic head carcinoma and pancreatic body carcinoma, as well as cholangiocarcinoma (CCA) as described above, e.g., common bile duct carcinoma and hilar cholangiocarcinoma, and gall bladder carcinoma.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications, whereas a length of about $50-1\times10^5$ nucleotides can be preferred for chromosomal probes and a length of about 25,000 to about 800,000 nucleotides can be preferred for locus-specific probes.

"Selectively hybridize to" (as well as "selective hybridization," "specifically hybridize to," and "specific hybridization"), in the context of the present disclosure, refers to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other non-target sequences. A "stringent hybridization" and "stringent hybridization wash conditions" in the context of nucleic acid hybridization (e.g., as in array, Southern hybridization, Northern hybridization, or FISH) are sequence-dependent, and differ under different conditions. An extensive guide to the hybridization of nucleic acids is found in, e.g., Tijssen, *Laboratory Techniques in Biochemistry and Molecular Biology—Hybridization with Nucleic Acid Probes*, Part I, Ch. 2, "Overview of principles of hybridization and the strategy of nucleic acid probe assays," Elsevier, NY (1993) ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids, which have more than 100 complementary residues, on an array or on a filter in a Southern or Northern blot is 42° C. using standard hybridization solutions (see, e.g., Sambrook and Russell, *Molecular Cloning: A Laboratory Manual,* 3rd ed., Vol. 1-3, Cold Spring Harbor Laboratory, Cold Spring Harbor Press, NY (2001)).

"Target sequence," "target region," and "nucleic acid target" refer to a nucleotide sequence that resides at a specific chromosomal location whose loss and/or gain, for example, is being determined.

The terminology used herein is for the purpose of describing particular embodiments only and is not otherwise intended to be limiting.

Methods of Detecting, Diagnosing, Prognosticating, Monitoring the Recurrence, and Monitoring the Efficacy of Therapeutic/Prophylactic Treatment of Pancreatobiliary Cancer A method of detecting high-grade dysplasia or pancreatobiliary cancer, or inferring increased risk thereof, in a patient is provided. The method comprises contacting a sample of pancreatobiliary cells from the patient with a set of detectably labeled probes comprising a locus-specific probe for MCL1 (myeloid cell leukemia sequence 1), a locus-specific probe for EGFR (epidermal growth factor receptor), a locus-specific probe for MYC, and a locus-specific probe for P16 under hybridization conditions and determining the presence of chromosomal abnormalities. Polysomy is indicative of high-grade dysplasia, pancreatobiliary cancer, or metastatic cancer to the pancreatobiliary tract, whereas tetrasomy, P16 loss, a single locus gain of MCL1, MYC or P16, or a single locus gain of MCL1, EGFR, or MYC with concurrent P16 loss infers increased risk of high-grade dysplasia, pancreatobiliary cancer, or metastatic cancer to the pancreatobiliary tract. In particular, polysomy (more than two copies of two or more loci per cell), such as in ≥4 cells, is indicative of high-grade dysplasia, pancreatobiliary cancer, or metastatic cancer to the pancreatobiliary tract, and tetrasomy (four copies of each locus), such as in ≥11 cells, or P16 loss (absence of 9p21), such as in at least 5% of cells, or a single locus gain (more than two copies of one locus per cell) of MCL1, MYC or P16 in ≥8 cells, or a single locus gain of MCL1, EGFR, or MYC with concurrent P16 loss in ≥4 cells infers increased risk of high-grade dysplasia, pancreatobiliary cancer, or metastatic cancer to the pancreatobiliary tract. The method can be used to distinguish cancer from an inflammatory benign condition, to identify a pre-cancerous lesion, to provide an early screening tool for primary sclerosing cholangitis (PSC) patients, who are known to be at risk for CCA, and to provide information about chromosomal abnormalities to aid therapeutic decisions and/or to provide prognostic information, as well as other benefits as described herein.

The sample of pancreatobiliary cells can be obtained by any suitable method. A preferred method is by brushing during endoscopic retrograde cholangiopancreatography (ERCP).

The above method can be carried out using any suitable detection method known in the art. Preferably, the above method is carried out using in situ hybridization, such as fluorescence in situ hybridization (FISH). Preferably, each probe is detectably labeled, and, when two or more probes are used simultaneously or sequentially on the same sample, preferably each probe is detectably labeled with a distinct label, such as a distinct fluorophore.

When the above methods are carried out by in situ hybridization, in which each probe is detectably labeled (and, when two or more probes are used simultaneously or sequentially on the same sample, distinctly labeled), such as by FISH, in which each probe is labeled (and, when two or more probes are used simultaneously or sequentially on the same sample, distinctly labeled) with a fluorophore, the methods can be carried out on a sample of pancreatobiliary cells, which are fresh (fresh cells can be cultured for 1-3 days and a blocker, such as Colcemid, can be added to the culture to block the cells in metaphase, during which chromosomes are highly condensed and can be visualized), frozen, or fixed (e.g., fixed in formalin and embedded in paraffin), treated (e.g., with RNase and pepsin) to increase accessibility of target nucleic acid (e.g., DNA) and reduce non-specific binding, and then subjected to hybridization with one or more probes, washing to remove any unbound probes, and detection of hybridized probes. For example, a cell suspension can be applied as a single layer onto a slide, and the cell density can be measured by a light or phase contrast microscope until the desired density of cells is attained. The slide can be submerged in 2× saline sodium citrate for 10 minutes at 37° C., 0.05% pepsin in HCl for 13 minutes at 37° C., PBS for five minutes at room temperature, 1% formaldehyde for five minutes at room temperature, and PBS for five minutes at room temperature, passed through graded alcohol, and dried. A section (approximately 5 μm in thickness) of a formalin-fixed, paraffin-embedded (FFPE) sample of pancreatobiliary cells can be mounted onto a slide, such as a SuperFrost Plus positively charged slide (available from ThermoShandon, Pittsburgh, Pa.), baked at 56° C. overnight, de-paraffinized, submerged in 1× saline sodium citrate, pH 6.3, at 80° C. for 35 minutes, and washed in water for three minutes. After protease digestion (4 mg pepsin/mL and 0.2 N HCl) at 37° C. for 15 minutes, the section can be rinsed in water for three minutes, passed through graded ethanol, and dried. Preferably, hybridization with one or more probes as described above using a FFPE section or slide with cell suspension (i.e., cytology slide) is carried out at 37° C. for 16-18 hours in an automated co-denaturation oven (HYBrite or ThermoBrite Denaturation/Hybridization System, Abbot Molecular, Inc., Des Plaines, Ill.) according to the manufacturer's instructions (such methods typically involve denaturation of probes and target nucleic acids). After hybridization, the section or cytology slide is preferably placed in washing buffer (2× saline sodium citrate/0.3% NP40; available from Abbott Molecular, Inc.) at room temperature for 2-10 minutes to remove the coverslip and then immersed in 73° C. washing buffer for two minutes, dried, and mounted with 4'6'-diamidino-2-phenylindole dihydrochloride hydrate (DAPI) I anti-fade solution (Abbott Molecular, Inc.). Preferably, the slide is analyzed with an epi-fluorescence microscope equipped with single band-pass filters (Abbott Molecular, Inc.).

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. Cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes, such as propidium iodide or 4,6-diamidino-2-phenylindole dihydrochloride (DAPI), usually following hybridization of probes to their target DNAs. Typically, neoplastic cells harbor nuclei that are enlarged, irregular in shape, and/or show a mottled staining pattern. Propidium iodide, typically used at a concentration of about 0.4 μg/ml to about 5 μg/ml, is a red-fluorescing DNA-specific dye that can be observed at an emission peak wavelength of 614 nm. DAPI, typically used at a concentration of about 125 ng/ml to about 1,000 ng/ml, is a blue fluorescing DNA-specific stain that can be observed at an emission peak wavelength of 452 nm with a DAPI filter at low magnification. In this case, only those cells pre-selected for detection are subjected to counting for chromosomal losses and/or gains. Preferably, pre-selected cells on the order of at least 100, and preferably more when there appear to be many cells with abnormal nucleic using the DAPI filter, are chosen for assessing chromosomal losses and/or gains.

Alternatively, an area in a tissue evidencing some level of dysplasia or a suspicious lesion can be localized using the DAPI filter at low magnification and thoroughly inspected for the presence of nuclei harboring abnormal copy numbers of any probe. In a normal cell, two copies of a given probe will be detected. In an abnormal cell, more or less copies of a given probe will be detected. Areas with the most significant copy number changes are preferably selected for enumeration. Wherever possible, numerous abnormal areas are selected and, within each abnormal area, at least about 10 random nuclei are analyzed under high power (64× or 100× objective) so that at least about 100 nuclei are analyzed. Preferably, nuclei are non-overlapping and harbor sufficiently bright signals.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

The copies of MCL1 (1q21), EGFR (7p12), MYC (8q24), and P16 (9p21) are counted.

Thus, such methods comprise contacting a sample of pancreatobiliary cells obtained from a patient, e.g., a nucleic acid sample, with a set of detectably labeled probes comprising a locus-specific probe for MCL1, a locus-specific probe for EGFR, a locus-specific probe for MYC, and a locus-specific probe for P16 under conditions that allow (or promote) the probe to bind selectively with its target nucleic acid sequence and form a stable hybridization complex. Such methods further comprise detecting the formation of hybridization complexes and counting the number of hybridization complexes. In view of the number of hybridization complexes comprising MCL1 (1q21), EGFR (7p12), MYC (8q24), and P16 (9p21), the method further comprises determining the copy number of MCL1 (1q21), EGFR (7p12), MYC (8q24), and P16 (9p21). If desired, the copy number can be compared to the expected or "normal" number of copies (i.e., 2 copies), wherein a copy number greater than 2 (i.e., for a gain) and a copy number less than 2 (i.e., for a loss), as appropriate, indicates that the cell is abnormal by FISH. The presence of more than two copies of two or more loci is indicative of polysomy. The presence of polysomy in ≥4 cells is indicative of high-grade dysplasia, pancreatobiliary cancer, or metastatic cancer to the pancreatobiliary tract. An increase in copy number of a single locus, such as more than two copies of a single locus, is indicative of a single locus gain. A gain of a single locus in ≥8 cells infers increased risk of high-grade dysplasia, pancreatobiliary cancer, or metastatic cancer to the pancreatobiliary tract. An increase in copy number of a single locus with concurrent P16 loss, such as more than two copies of a single locus and zero or one copy of P16, is indicative of a single locus gain with concurrent P16 loss. A gain of a single locus with concurrent P16 loss in >4 cells infers increased risk of high-grade dysplasia, pancreatobiliary cancer, or metastatic cancer to the pancreatobiliary tract. The presence of four copies of all loci is indicative of tetrasomy. The presence of tetrasomy in ≥11 cells infers increased risk of high-grade dysplasia, pancreatobiliary cancer, or metastatic cancer to the pancreatobiliary tract. Absence of P16 signals is indicative of P16 loss. The absence of P16 in at least 5% of cells infers increased risk of high-grade dysplasia, pancreatobiliary cancer, or metastatic cancer to the pancreatobiliary tract.

While deparaffinization, pretreatment, staining, and routine slide washing also can be conducted in accordance with methods known in the art, use of an automated system, however, such as the VP 2000 Process (Abbott Molecular, Inc., Des Plaines, Ill.), decreases the amount of time needed to prepare slides for evaluation. Slides can be prepared in large batches (e.g., 50 slides), as opposed to small batches (e.g., 4 slides) when standard Coplin jars are used for post-hybridization washing. In addition, the scoring of slides can be fully automated using automated imaging, thereby reducing the amount of hands-on time required for specimen analysis. Full automation also enables the use of an imaging algorithm that captures more abnormal cells more frequently and consistently. Also, while any suitable method of slide preparation known in the art can be used, slides are preferably prepared using ThinPrep 2000 (Hologic, Inc., Bedford, Mass.), which generates more uniform and consistent monolayers of cells.

Other methods already known in the art or currently under development may require or prefer the use of a sample of pancreatobiliary cells that is other than cells fixed in formalin and embedded in paraffin, e.g., fresh or frozen cells, homogenized cells, lysed cells, or isolated or purified nucleic acids (e.g., a "nucleic acid sample" such as DNA) from pancreatobiliary cells ("sample of pancreatobiliary cells" as used herein is intended to encompass all forms of a sample of pancreatobiliary cells that enable the determination of copy number and gain/loss). Nuclei also can be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution, such as formaldehyde.

Examples of methods that can be used herein include, but are not limited to, quantitative polymerase chain reaction (Q-PCR), real-time Q-PCR (Applied Biosystems, Foster City, Calif.), densitometric scanning of PCR products, digital PCR, optionally with pre-amplification of the gene(s) and/or chromosomal region(s) for which copy number(s) is/are to be determined (see, e.g., Vogelstein et al., PNAS USA 96: 9236-9241 (1999); U.S. Pat. App. Pub. No. 2005/0252773; and U.S. Pat. App. Pub. No. 2009/0069194), comparative genomic hybridization (CGH; see, e.g., Kallioniemi et al., Science 258: 818-821 (1992); and Int'l Pat. App. Pub. No. WO 93/18186), microsatellite or Southern allelotype analysis, dot blots, arrays, microarrays (Carter, Nature Genetics Supplement 39: S16-S21 (July 2007)), multiplex amplifiable probe hybridization (MAPH), multiplex ligation-dependent probe amplification (MLPA; see, e.g., Schouten et al., Nucleic Acids Res. 30: e 57 (2002)), denaturing high performance liquid chromatography (dHPLC; Kumar et al., J. Biochem. Biophys. Methods 64(3): 226-234 (2005)), dynamic allele-specific hybridization (DASH), measuring fluorescent probe lengths on combed genomic DNA (Herrick et al., PNAS 97(1): 222-227 (2000)), reference query pyrosequencing (RQPS; Liu et al., Cold Spring Harb. Protoc. doi: 10.1101/pdb.prot5491 (2010)), mapping of fosmid ends onto a reference sequence (capillary-based technology), microelectrophoretic and nanopore sequencing (see, e.g., Service, Science 311: 1544-1546 (2006); and Shendure et al., Nat. Rev. Genet. 5: 335-344 (2004)), and the like.

Denaturation of nucleic acid targets for analysis by in situ hybridization and similar methods typically is done in such a manner as to preserve cell morphology. For example, chromosomal DNA can be denatured by high pH, heat (e.g., temperatures from about 70-95° C.), organic solvents (e.g., formamide), and combinations thereof. Probes, on the other hand, can be denatured by heat in a matter of minutes.

After denaturation, hybridization is carried out. Conditions for specifically hybridizing the probes to their nucleic acid targets generally include the combinations of conditions that are employable in a given hybridization procedure to produce specific hybrids, the conditions of which may easily be determined by one of ordinary skill in the art. Such conditions typically involve controlled temperature, liquid phase, and contact between a probe and a target. Hybridization conditions vary depending upon many factors including probe concentration, target length, target and probe G-C content, solvent composition, temperature, and duration of incubation. At least one denaturation step can precede contact of the probes with the targets. Alternatively, the probe and the target can be subjected to denaturing conditions together while in contact with one another, or with subsequent contact of the probe with the biological sample. Hybridization can be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, a blocking agent, such as unlabeled blocking nucleic acid, as described in U.S. Pat. No. 5,756,696 (the contents of which are herein incorporated by reference in their entirety, and specifically for the description of the use of blocking nucleic acid), can be used. Other conditions can be readily employed for specifically hybridizing the probes to their nucleic acid targets present in the sample, as would be readily apparent to one of skill in the art. Hybridization protocols are described, for example, in Pinket et al., PNAS USA 85: 9138-9142 (1988); In situ Hybridization Protocols, Methods in Molecular Biology, Vol. 33, Choo, ed., Humana Press, Totowa, N.J. (1994); and Kallioniemi et al., PNAS USA 89: 5321-5325 (1992).

Upon completion of a suitable incubation period, non-specific binding of chromosomal probes to sample DNA can be removed by a series of washes. Temperature and salt concentrations are suitably chosen for a desired stringency. The level of stringency required depends on the complexity of a specific probe sequence in relation to the genomic sequence, and can be determined by systematically hybridizing probes to samples of known genetic composition. In general, high stringency washes can be carried out at a temperature in the range of about 65 to about 80° C. with about 0.2× to about 2×SSC and about 0.1% to about 1% of a non-ionic detergent, such as Nonidet P-40 (NP40). If lower stringency washes are required, the washes can be carried out at a lower temperature with an increased concentration of salt.

When fluorophore-labeled probes or probe compositions are used, the detection method can involve fluorescence microscopy, flow cytometry, or other means for determining probe hybridization. Any suitable microscopic imaging method can be used in conjunction with the methods described herein for observing multiple fluorophores. In the case where fluorescence microscopy is employed, hybridized samples can be viewed under light suitable for excitation of each fluorophore and with the use of an appropriate filter or filters. Automated digital imaging systems, such as the MetaSystems, BioView or Applied Imaging systems, alternatively can be used, along with signal enumeration and data acquisition algorithms.

Depending on the method employed, a digital image analysis system can be used to facilitate the display of results and to improve the sensitivity of detecting small differences in fluorescence intensity. An exemplary system is QUIPS (an acronym for quantitative image processing system), which is an automated image analysis system based on a standard fluorescence microscope equipped with an automated stage, focus control and filter wheel (Ludl Electronic Products, Ltd., Hawthorne, N.Y.). The filter wheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display, which is used for finding interesting areas on a slide as well as for focusing. The other camera port has a cooled CCD camera (model 200 by Photometrics Ltd., Tucson, Ariz.), which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In array CGH (aCGH) the probes are immobilized at distinct locations on a substrate and are not labeled (see, e.g., Int'l Pat. App. Pub. No. WO 96/17958). Instead, sample nucleic acids, which comprise target nucleic acid(s), are labeled. Either the sample nucleic acids are labeled prior to hybridization or the hybridization complexes are detectably labeled. In dual- or multi-color aCGH the probe array is simultaneously or sequentially hybridized to two or more collections of differently labeled target nucleic acids.

The above methods can be used in the prognosis of pancreatobiliary cancer, the monitoring of the efficacy of the prophylactic or therapeutic treatment (e.g., the administration of tyrosine kinase inhibitors to patients with tumors that over-express EGFR) of pancreatobiliary cancer, and the monitoring of the recurrence of pancreatobiliary cancer. The methods can be used to confirm results obtained with other detection methods. The risk of cancer in patients with pre-cancerous lesions can be assessed using such methods, as well as the aggressiveness of the cancer (e.g., more chromosomal abnormalities and/or more widespread chromosomal abnormalities in the field effect cells). Such methods also can be used to aid in treatment decisions, e.g., active surveillance, surgery, or therapy (e.g., the administration of tyrosine kinase inhibitors to patients with tumors that over-express EGFR), and adjuvant treatment decisions. If desired, the methods described herein can be used in conjunction with other tests, such as routine cytology, histology, prostate-specific antigen (PSA) assay, nomogram, methylation, mutation, and the like.

Thus, the method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a sample of pancreatobiliary cells for chromosomal abnormalities. Generally, in making such a comparison, the predetermined level is obtained by running a particular assay a sufficient number of times and under appropriate conditions such that a linkage or association of a particular chromosomal abnormality (presence or level) with a particular stage or endpoint of a disease, disorder or condition or with particular indicia can be made. Typically, the predetermined level is obtained with assays of reference subjects (or populations of subjects).

In particular, with respect to a predetermined level as employed for monitoring disease progression and/or treatment, the chromosomal abnormality (presence or level) may be "unchanged," "favorable" (or "favorably altered"), or "unfavorable" (or "unfavorably altered"). "Elevated" or "increased" refers to a level of chromosomal abnormality in a sample of pancreatobiliary cells that is higher than a typical or normal level or range (e.g., predetermined level), or is higher than another reference level or range (e.g., earlier or baseline sample). The term "lowered" or "reduced" refers to a level of chromosomal abnormality in a sample of pancreatobiliary cells that is lower than a typical or normal level or range (e.g., predetermined level), or is lower than another reference level or range (e.g., earlier or baseline sample). The term "altered" refers to a level of chromosomal abnormality in a sample of pancreatobiliary cells that is altered (increased or decreased) over a typical or normal level or range (e.g., predetermined level), or over another reference level or range (e.g., earlier or baseline sample).

The typical or normal level or range for a given chromosomal abnormality is defined in accordance with standard practice. Because the levels of chromosomal abnormalities in some instances will be very low, a so-called altered level or alteration can be considered to have occurred when there is any net change as compared to the typical or normal level or range, or reference level or range, which cannot be explained by experimental error or sample variation. Thus, the level measured in a particular sample will be compared with the level or range of levels determined in similar samples from a so-called normal subject. In this context, a "normal subject" is an individual with no detectable disease, and a "normal" or "control" patient or population is/are one(s) that exhibit(s) no detectable disease, respectively, for example. Furthermore, given that chromosomal abnormalities are not routinely found at high levels in the majority of the human population, a "normal subject" can be considered an individual with no substantial detectable increased level of a given chromosomal abnormality, and a "normal" (sometimes termed "control") patient or population is/are one(s) that exhibit(s) no substantial detectable increased level of a given chromosomal abnormality. An "apparently normal subject" is one in which chromosomal abnormalities have not been or are being assessed. The level of a given chromosomal abnormality is said to be "elevated" when the chromosomal abnormality is normally undetectable, but is detected in a test sample, as well as when the analyte is present in the test sample at a higher than normal level. Thus, inter alia, the disclosure provides a method of screening for a subject having, or at risk of having, pancreatobiliary cancer.

The method can also involve the detection of other markers and the like.

The methods described herein also can be used to determine whether or not a subject has or is at risk of developing pancreatobiliary cancer. Specifically, such a method can comprise the steps of:

(a) determining chromosomal abnormalities in a sample of pancreatobiliary cells from a subject (e.g., using the methods described herein, or methods known in the art); and (b) comparing the levels of chromosomal abnormalities determined in step (a) with predetermined levels, wherein, if the levels of chromosomal abnormalities determined in step (a) are favorable with respect to predetermined levels, then the subject is determined to be at less risk of having pancreatobiliary cancer. However, if the levels of chromosomal abnormalities determined in step (a) are unfavorable with respect to predetermined levels, then the subject is determined to have or be at risk for pancreatobiliary cancer.

Additionally, provided herein is method of monitoring the progression of pancreatobiliary cancer in a subject. Optimally, the method comprises the steps of:

(a) determining chromosomal abnormalities in a sample of pancreatobiliary cells from a subject;

(b) determining the levels of chromosomal abnormalities in a later sample of pancreatobiliary cells from the subject; and (c) comparing the levels of chromosomal abnormalities as determined in step (b) with the levels of chromosomal abnormalities as determined in step (a), wherein if the levels in step (b) are unchanged or unfavorable when compared to the levels determined in step (a), then pancreatobiliary cancer is determined to have continued, progressed or worsened in the subject. By comparison, if the levels as determined in step (b) are favorable when compared to the levels as determined in step (a), then pancreatobiliary cancer is likely to have discontinued, regressed or improved in the subject.

Optionally, the method further comprises comparing the levels of chromosomal abnormalities as determined in step (b), for example, with predetermined levels. Further, optionally the method comprises treating the subject, e.g., with one or more pharmaceutical compositions, radiation, and/or hormone therapy, for a period of time if the comparison shows that the levels as determined in step (b), for example, are unfavorably altered with respect to the predetermined levels.

Still further, the methods can be used to monitor treatment in a subject receiving treatment, e.g., with one or more pharmaceutical compositions, radiation, and/or hormone therapy. Specifically, such methods involve providing a first sample of pancreatobiliary cells from a subject before the subject has been treated. Next, the levels of chromosomal abnormalities in the first sample of pancreatobiliary cells are determined (e.g., using the methods described herein or as known in the art). After the levels of chromosomal abnormalities are determined, optionally the levels are then compared with predetermined levels. If the levels as determined in the first sample of pancreatobiliary cells are lower than the predetermined levels, then the subject is not treated. However, if the levels as determined in the first sample of pancreatobiliary cells are higher than the predetermined levels, then the subject is treated for a period of time. The period of time that the subject is treated can be determined by one skilled in the art (for example, the period of time can be from about seven (7) days to about two years, preferably from about fourteen (14) days to about one (1) year).

During the course of treatment, second and subsequent samples of pancreatobiliary cells are then obtained from the subject. The number of samples and the time in which said samples are obtained from the subject are not critical. For example, a second sample could be obtained seven (7) days after the subject is first treated, a third sample could be obtained two (2) weeks after the subject is first treated, a fourth sample could be obtained three (3) weeks after the subject is first treated, a fifth sample could be obtained four (4) weeks after the subject is first treated, etc.

After each second or subsequent sample is obtained from the subject, the levels of chromosomal abnormalities in the second or subsequent sample are determined (e.g., using the methods described herein or as known in the art). The levels as determined in each of the second and subsequent samples are then compared with the levels as determined in the first sample (e.g., the sample that was originally optionally compared to the predetermined level). If the levels as determined in step (c) are favorable when compared to the levels as determined in step (a), then pancreatobiliary cancer is likely to have discontinued, regressed or improved, and the subject should continue to be treated. However, if the levels determined in step (c) are unchanged or unfavorable when compared to the levels as determined in step (a), then pancreatobiliary cancer is determined to have continued, progressed or worsened, and the subject should be treated with a higher dosage of pharmaceutical composition, radiation, or hormone, for example, or the subject should be treated differently.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained.

Moreover, the present disclosure also relates to methods of determining whether a subject predisposed to or suffering from pancreatobiliary cancer will benefit from treatment. In particular, the disclosure relates to companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, pancreatobiliary cancer is a candidate for therapy. Generally, the subject is one who has experienced some symptom of the disease or who has actually been diagnosed as having, or being at risk for, such a disease, and/or who demonstrates unfavorable levels of chromosomal abnormalities, as described herein.

The method optionally comprises an assay as described herein, where levels of chromosomal abnormalities are assessed before and following treatment of a subject. The observation of unfavorable levels of chromosomal abnormalities following treatment confirms that the subject will not benefit from receiving further or continued treatment, whereas the observation of favorable levels of chromosomal abnormalities following treatment confirms that the subject will benefit from receiving further or continued treatment. This confirmation assists with management of clinical studies, and provision of improved patient care.

Probes

A set of probes is also provided. The set of probes comprises, or consists of, a locus-specific probe for MCL1 (myeloid cell leukemia sequence 1), a locus-specific probe for EGFR (epidermal growth factor receptor), a locus-specific probe for MYC, and a locus-specific probe for P16.

Suitable probes for use as locus-specific probes hybridize to a specific region on a chromosome containing a gene. The locus-specific probe for the gene MCL1 (1q21) can hybridize to all or a portion of the MCL1 gene at q21 on chromosome 1 (i.e., 1q21). Recently published studies regarding the gene MCL1 indicate that this gene mediates TRAIL (tumor necrosis factor-related apoptosis-inducing ligand) resistance in CCA cells (Werneburg et al., J. Biol. Chem. 282(30): 28960-28970 (2007)). TRAIL is a promising agent for cancer therapy and, therefore, MCL1 status of a patient's tumor may be valuable information for therapeutic decisions.

The locus-specific probe for EGFR can hybridize to all or a portion of the EGFR gene at p12 on chromosome 7 (i.e., 7p12). EGFR has been successfully targeted by tyrosine kinase inhibitors in a subset of patients with non-small cell lung cancer and advanced pancreatic cancer (DeHaan et al., Hum. Pathol. 38(3): 491-499 (March 2007)) and, therefore, is another gene of potential therapeutic importance in the context of pancreatobiliary carcinoma. Furthermore, EGFR is located on chromosome 7, and gain of chromosome 7 (i.e., trisomy 7) in pancreatobiliary cells has been shown to be a risk factor for the presence of malignancy, since approximately half of patients with trisomy 7 are diagnosed with carcinoma (Fritcher et al. (2009), supra; Moreno Luna et al., Gastroenterology 131(4): 1064-1072 (2006)).

The locus-specific probe for MYC (8q24) can hybridize to all or a portion of the MYC gene at q24 on chromosome 8 (i.e., 8q24). The locus-specific probe for the P16 gene (9p21) can hybridize to all or a portion of the P16 gene at p21 on chromosome 9 (i.e., 9p21).

Suitable probes for use as chromosomal probes hybridize with repetitive DNA associated with the centromere of a chromosome. Centromeres of primate chromosomes contain a complex family of long-tandem repeats of DNA, which are composed of a monomer repeat length of about 171 base pairs (bp), that is referred to as α-satellite DNA. Chromosomal probes are typically about $50–1\times10^5$ nucleotides in length. Longer probes typically comprise smaller fragments of about 100-500 nucleotides in length.

Chromosome enumerator probes (CEP) and locus-specific probes that target a chromosome region or sub-region can be obtained commercially or readily prepared by those in the art. Such probes can be commercially obtained from Abbott Molecular, Inc. (Des Plaines, Ill.), Molecular Probes, Inc. (Eugene, Oreg.), or Cytocell (Oxfordshire, UK). Chromosomal probes can be prepared, for example, from protein nucleic acids (PNA), cloned human DNA such as plasmids, bacterial artificial chromosomes (BACs), and P1 artificial chromosomes (PACs) that contain inserts of human DNA sequences. A region of interest can be obtained via PCR amplification or cloning. In another embodiment, the chromosomal probes can be oligo probes. Alternatively, chromosomal probes can be prepared synthetically in accordance with methods known in the art.

When targeting of a particular gene locus is desired, probes that hybridize along the entire length of the targeted gene can be preferred, although not required. A locus-specific probe can be designed to hybridize to an oncogene or tumor suppressor gene, the genetic aberration of which is correlated with metastasis, e.g., MYC.

The probes can be prepared by any method known in the art. Probes can be synthesized or recombinantly produced. Such probes can range in length from about 25,000 base pairs to about 800,000 base pairs.

Preferably, probes are detectably labeled, and, when two or more probes are used simultaneously or sequentially on the same sample, preferably each probe is distinctly labeled. Preferably, the probes are detectably labeled with fluorophores. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethyl-4-bora-3a,4a-diaza-3-indacenepropionic acid, eosin-5-isothiocyanate, erythrosine-5-isothiocyanate, SpectrumRed (Abbott Molecular, Inc.), SpectrumGold (Abbott Molecular, Inc.), SpectrumGreen (Abbott Molecular, Inc.), SpectrumAqua (Abbott Molecular, Inc.), TEXAS RED (Molecular Probes, Inc.), Lucifer yellow, and CASCADE blue acetylazide (Molecular Probes, Inc.). The particular label used is not critical; desirably, however, the particular label does not interfere with in situ hybridization of the probe and the detection of label on any other probe. The label desirably is detectable in as low copy number as possible to maximize the sensitivity of the assay and be detectable above any background signal. Also desirably, the label provides a highly localized signal, thereby providing a high degree of spatial resolution.

Attachment of fluorophores to nucleic acid probes is well-known in the art and can be accomplished by any available means. Fluorophores can be covalently attached to a particular nucleotide, for example, and the labeled nucleotide incorporated into the probe using standard techniques such as nick translation, random priming (Rigby et al., J. Mol. Biol. 113: 237 (1997)), PCR labeling, end labeling, direct labeling by chemical modification of particular residues, such as cytosine residues (U.S. Pat. No. 5,491,224), and the like. Alternatively, the fluorophore can be covalently attached to nucleotides with activated linker arms, which have been incorporated into the probe, for example, via a linker to the deoxycytidine nucleotides of the probe that have been transaminated. Methods for labeling probes are described in U.S. Pat. No. 5,491,224, and Morrison et al., Molecular Cytogenetics: Protocols and Applications, Chapter 2, "Labeling Fluorescence In Situ Hybridization Probes for Genomic Targets," pp. 21-40, Fan, Ed., Humana Press (2002), both of which are herein incorporated by reference for their descriptions of labeling probes.

One of skill in the art will recognize that other agents or dyes can be used in lieu of fluorophores as label-containing moieties. Luminescent agents include, for example, radioluminescent, chemiluminescent, bioluminescent, and phosphorescent label-containing moieties. Agents that are detectable with visible light include cyanin dyes. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes can be achieved as described below.

Chromosomal probes hybridized to target regions alternatively can be visualized by enzymatic reactions of label moieties with suitable substrates for the production of insoluble color products. Each probe can be discriminated from other probes within the set by choice of a distinct label moiety. A biotin-containing probe within a set can be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzoate serves as a substrate for HRP.

Kit

Also provided is a kit. The kit comprises (a) a set of probes that enables detection of pancreatobiliary cancer in a patient and (b) instructions for detecting, diagnosing, prognosticating, or assessing the therapeutic/prophylactic treatment of pancreatobiliary cancer in a patient. Thus, the kit can comprise (a) a set of probes that enables detection of pancreatobiliary cancer in a patient, wherein the set of probes comprises, or consists of, a locus-specific probe for MCL1 (myeloid cell leukemia sequence 1), a locus-specific probe for EGFR (epidermal growth factor receptor), a locus-specific probe for MYC, and a locus-specific probe for P16 and (b) instructions for detecting pancreatobiliary cancer in a patient, wherein the instructions comprise determining in a sample of pancreatobiliary cells obtained from the patient the presence of chromosomal abnormalities, wherein polysomy is indicative of high-grade dysplasia, pancreatobiliary cancer, or metastatic cancer to the pancreatobiliary tract and tetrasomy, P16 loss, a single locus gain of MCL1, MYC or P16, or a single locus gain of MCL1, EGFR, or MYC with concurrent P16 loss infers an increased risk of high-grade dysplasia, pancreatobiliary cancer, or metastatic cancer to the pancreatobiliary tract. In particular, polysomy (more than two copies/cell of two or more loci), such as in ≥4 cells, is indicative of high-grade dysplasia, pancreatobiliary cancer, or metastatic cancer to the pancreatobiliary tract. A single locus gain (more than two copies/cell) of MCL1, MYC or P16, such as in ≥8 cells, a single locus gain of MCL1, EGFR, or MYC with concurrent P16 loss, such as in >4 cells, or tetrasomy (four copies of each locus), such as in ≥11 cells, or P16 loss (absence of P16), such as in at least 5% of cells, infers increased risk of high-grade dysplasia, pancreatobiliary cancer, or metastatic cancer to the pancreatobiliary tract. Such kits may further comprise blocking agents or other probes, various labels or labeling agents to facilitate detection of the probes, reagents for hybridization (e.g., buffers), a metaphase spread, and the like.

EXAMPLES

The following examples serve to illustrate the present disclosure. The examples are not intended to limit the scope of the claimed invention in any way.

Example 1

This example describes the selection of candidate probes.

A literature review was performed to identify common chromosomal alterations found in pancreatobiliary tumors based on multiple comparative genomic hybridization (CGH) studies (Miller et al., J. Exp. Clin. Cancer Res. 28: 62 (2009); Shiraishi et al., Oncology 60(2): 151-161 (2001); and Lee et al., J. Korean Med. Sci. 19(5): 682-687 (2004)). New probes were designed and manufactured. UroVysion™ (Abbott Molecular, Des Plaines, Ill.), a commercially available probe set, was also evaluated for comparision. The first probe set consisted of a locus-specific probe for EGFR (7p12) labeled with SpectrumRed™, a locus-specific probe for MYC (8q24) labeled with SpectrumGreen, a locus-specific probe for P16 (9p21) labeled with SpectrumGold™, and a centromeric probe for chromosome 9 (chromosome enumerator probe 9 (CEP9®)) labeled with SpectrumAqua™. The second probe set consisted of a locus-specific probe for P53 (17p13) labeled with SpectrumRed™, a centromeric probe for chromosome 17 (CEP17®) labeled with SpectrumAqua™, a locus-specific probe for ERBB2 (17q11) labeled with SpectrumGreen™, and a locus-specific probe for AURKA (20q13) labeled with SpectrumGold™. The third probe set consisted of a locus-specific probe for MCL1 (myeloid cell leukemia sequence 1; 1q21.2) labeled with SpectrumRed™, a locus-specific probe for D5S721 (5p15) labeled with SpectrumAqua™, a locus-specific probe for CCND1 (cyclin D1; 11q13) labeled with SpectrumGold™, and a locus-specific probe for TEL (12p13) labeled with SpectrumGreen. The UroVysion™ probe set consists of a centromeric probe for chromosome 3 (CEP3®) labeled with SpectrumRed™, a centromeric probe for chromosome 7 (CEP7®) labeled with SpectrumGreen™, a locus-specific probe for P16 (9p21) labeled with SpectrumGold™, and a centromeric probe for chromosome 17 (CEP17®) labeled with SpectrumAqua™.

A probe selection study was performed to evaluate probe quality and accuracy in detecting pancreatobiliary carcinoma. While the intended clinical application of this assay is pancreatobiliary brushings obtained during ERCP, tumor resection specimens were evaluated because cells of interest are reliably present in large numbers. Archived formalin-fixed paraffin-embedded (FFPE) liver (n=14), bile duct (n=1), and pancreas (n=14) resections containing carcinoma were identified. Each resection was from a unique patient. Four slides were prepared for each case for FISH analysis. The corresponding H&E (hematoxylin and eosin) slide was microscopically evaluated by a pathologist, and areas of interest (tumor and benign ducts) were marked. Of the 29 resections, 16 areas of CCA (two areas were from the same resection/patient) and 14 areas of pancreatic adenocarcinoma were identified. Nine benign ducts were identified within nine resection specimens. The areas of interest were concurrently marked on the unstained tissue slides and hybridized with the three candidate FISH probe sets and UroVysion™. A separate slide was used for each probe set. Hybridized slides were evaluated using a fluorescence microscope equipped with filters for visualizing each of the four probe fluorophores. The area of interest was located on the FISH slide, and 50 cells were evaluated within that area. The number of signals for each of the four probes was recorded per cell.

All probes were of high quality except for the locus-specific probe for P53 (17p13). The probe was very small and non-specific. Therefore, it was often difficult to differentiate and evaluate.

The locus gains observed in paraffin-embedded tumor specimens is shown in FIG. 1, which is a bar graph of percent of cells vs. probe. The proportion of cells with copy number gain (>2 copies per cell) out of 1,500 tumor cells was evaluated for each probe. The proportion of cells with copy number gain (>2 copies per cell) out of 300 normal cells was evaluated for each probe. As shown in FIG. 1, the five probes that demonstrated the highest proportion of gain in tumor specimens included 8q24, 1q21, 7p12, 17q12, and 11q13.

The mean probe copy number observed per probe is shown in FIG. 2. As shown in FIG. 2, the five probes that demonstrated the highest mean copy number included 8q24, 17q12, 20q13, 1q21, and 7p12.

The proportion of cells with homozygous loss is shown in FIG. 3. The proportion of tumor cells with homozygous loss of each locus (0 copies per cell) out of 1,500 tumor cells was evaluated for each probe. The proportion of normal cells with homozygous loss of each locus (0 copies per cell) out of 300 normal cells was evaluated for each probe. As shown in FIG. 3, the probe that showed the highest proportion of cells with homozygous loss was 9p21. Over 40% of carcinoma cells in this study had homozygous loss.

A statistical analysis was performed to determine the optimal cut-off values for the detection of carcinoma using the signal patterns from all recorded cells. The nine benign ducts were used to represent the number of signals present in normal pancreatobiliary tissue. ROC (receiver operating characteristic) analyses were performed to determine cut-off values that best discriminated chromosomal abnormalities (gains and losses) in tumor cells from cells with normal chromosomal content for each probe with no false positives (i.e., specificity of 100%) as shown in Table 1. In order to be conservative, the cut-off for 1q21 and 11q13 was increased from 2% (1 cell) to 4% (2 cells).

TABLE 1

Cut-off values for each probe on paraffin-embedded tumor specimens

| Probe Locus | Cut-Off (%) | Gain or Loss |
|---|---|---|
| 1q21 | 4 | Gain |
| CEP3 ® | 8 | Gain |
| 5p15 | 8 | Gain |
| 7p12 | 18 | Gain |
| CEP7 ® | 38 | Gain |
| 8q24 | 24 | Gain |
| 9p21 | 14 | Homozygous Loss |
| 9p21 (UroVysion) | 11 | Homozygous Loss |
| CEP9 ® | 8 | Gain |
| 11q13 | 4 | Gain |
| 12p13 | 18 | Gain |
| 17p13 | 8 | Homozygous Loss |
| CEP17 ® | 10 | Gain |
| CEP17 ® (UroVysion) | 4 | Gain |
| 17q12 | 10 | Gain |
| 20q13 | 10 | Gain |

Based on the above, the locus-specific probe for P16 (9p21) was selected. The next step of probe selection statistical analysis was to calculate the sensitivity of various oncogenic probe combinations of three probes using the established cut-offs from Table 1 with a target specificity of 100%. Table 2 lists the performance of 25 probe combinations with high sensitivity, as well as UroVysion™ (CEP3®, CEP7®, and CEP17®) for comparision. The sensitivity of each probe set with the addition of the locus-specific probe for P16 (9p21) is shown.

Example 2

This example describes the analysis of ERCP brushings using the FISH probes selected in Example 1.

The aim of this study was to select cut-offs for considering a specimen abnormal by FISH using pancreatobiliary brushing specimens from patients with clinicopathologic follow-up. Performance of the new probe set for the detection of malignancy will be subsequently compared to the performance of UroVysion™.

TABLE 2

Sensitivity of various three-probe combinations of oncogene loci and sensitivity with addition of locus-specific probe for P16 (9p21) with target specificity of 100%

| Combo ID | Oncogene Locus 1 (gain) | Oncogene Locus 2 (gain) | Oncogene Locus 3 (gain) | Oncogene Locus 4 (loss) | Sensitivity (%) of 3 loci (oncogenic only) N = 30 | Sensitivity (%) of 4 loci (oncogenic and 9p21) N = 30 | Specificity N = 9 |
|---|---|---|---|---|---|---|---|
| 28 | 1q21 | 17q12 | 11q13 | 9p21 | 28 (93.3) | 29 (96.7) | 9 (100) |
| 16 | 1q21 | 7p12 | 11q13 | 9p21 | 27 (90.0) | 29 (96.7) | 9 (100) |
| 22 | 1q21 | 8q24 | 11q13 | 9p21 | 27 (90.0) | 29 (96.7) | 9 (100) |
| 32 | 7p12 | 8q24 | 11q13 | 9p21 | 27 (90.0) | 29 (96.7) | 9 (100) |
| 18 | 1q21 | 7p12 | 17q12 | 9p21 | 27 (90.0) | 28 (93.3) | 9 (100) |
| 24 | 1q21 | 8q24 | 17q12 | 9p21 | 27 (90.0) | 28 (93.3) | 9 (100) |
| 26 | 1q21 | 17q12 | 5p15 | 9p21 | 27 (90.0) | 28 (93.3) | 9 (100) |
| 27 | 1q21 | 17q12 | 7p12 | 9p21 | 27 (90.0) | 28 (93.3) | 9 (100) |
| 29 | 1q21 | 17q12 | 12p13 | 9p21 | 27 (90.0) | 28 (93.3) | 9 (100) |
| 30 | 1q21 | 17q12 | 20q | 9p21 | 27 (90.0) | 28 (93.3) | 9 (100) |
| 34 | 7p12 | 8q24 | 17q12 | 9p21 | 27 (90.0) | 28 (93.3) | 9 (100) |
| 19 | 1q21 | 7p12 | 20q | 9p21 | 26 (86.7) | 28 (93.3) | 9 (100) |
| 25 | 1q21 | 8q24 | 20q | 9p21 | 26 (86.7) | 28 (93.3) | 9 (100) |
| 14 | 1q21 | 7p12 | 5p15 | 9p21 | 26 (86.7) | 28 (93.3) | 9 (100) |
| 15* | 1q21 | 7p12 | 8q24 | 9p21 | 26 (86.7) | 28 (93.3) | 9 (100) |
| 17 | 1q21 | 7p12 | 12p13 | 9p21 | 26 (86.7) | 28 (93.3) | 9 (100) |
| 20 | 1q21 | 8q24 | 5p15 | 9p21 | 26 (86.7) | 28 (93.3) | 9 (100) |
| 21 | 1q21 | 8q24 | 7p12 | 9p21 | 26 (86.7) | 28 (93.3) | 9 (100) |
| 23 | 1q21 | 8q24 | 12p13 | 9p21 | 26 (86.7) | 28 (93.3) | 9 (100) |
| 31 | 7p12 | 8q24 | 5p15 | 9p21 | 26 (86.7) | 28 (93.3) | 9 (100) |
| 33 | 7p12 | 8q24 | 12p13 | 9p21 | 26 (86.7) | 28 (93.3) | 9 (100) |
| 37 | 7p12 | 17q12 | 11q13 | 9p21 | 25 (83.3) | 29 (96.7) | 9 (100) |
| 36 | 7p12 | 17q12 | 5p15 | 9p21 | 25 (83.3) | 28 (93.3) | 9 (100) |
| UroVysion | CEP3 | CEP7 | CEP17 | 9p21 | 24 (80.0) | 29 (96.7) | 9 (100) |
| 35 | 7p12 | 8q24 | 20q | 9p21 | 23 (76.7) | 27 (90.0) | 9 (100) |
| 38 | 7p12 | 17q12 | 12p13 | 9p21 | 22 (73.3) | 27 (90.0) | 9 (100) |

*final probe set

TABLE 3

Sensitivity of final probe set as the number of probes is increased with respective number of specimens positive for all probes

| Probe(s) | Sensitivity N (%) | No. of specimens "+" by all probes |
|---|---|---|
| 7p12 | 17 (56.8) | 17 |
| 7p12 + 8q24 | 20 (66.7) | 15 |
| 7p12 + 8q24 + 1q21 | 26 (86.7) | 15 |
| 7p12 + 8q24 + 1q21 + 9p21 | 28 (93.3) | 3 |

The locus-specific probe for MYC (8q24) detected gains with the highest copy number most frequently in comparison to all other probes analyzed. The probe set including MCL1 (1q21), EGFR (7p12), MYC (8q24), and P16 (9p21) had a higher sensitivity (86.7%) than the centromeric probes of UroVysion™ (80.0%). The sensitivity of this probe set (93.3%) detected only one less case of carcinoma than UroVysion™ (96.7%).

Patients with pancreatobiliary strictures suspicious for carcinoma underwent ERCP as part of clinical practice at Mayo Clinic during which a stricture brushing was obtained and submitted to the Molecular Cytology Laboratory. Brushings were formulated into cell pellets, and FISH analysis was performed using the UroVysion™ probe set. Residual cell pellet, if present, was archived in the laboratory. Specimens from 97 unique patients whose brushings had been consecutively received in the Mayo Clinic Molecular Cytology Laboratory in 2005 were retrospectively identified. Inclusion criteria were: (a) definitive classification of the stricture as benign or malignant on follow-up, (b) available residual cell pellet, and (c) at least one year of clinical follow-up for patients without carcinoma. The gold standard for carcinoma included pathologic evidence (e.g., biopsy, fine-needle aspiration (FNA), or routine cytology) and/or clinical evidence (tumor or mass on imaging, progression of cancer with obvious metastasis) of malignancy. For patients with more than one specimen from separate ERCP procedures, only the earliest/first brushing was used for analysis. If the earliest brushing specimen was unavailable, the brushing from the next consecutive visit was utilized.

A final probe mixture containing the four FISH probes selected in Example 1 was generated in the following formulation: MCL1 (1q21) labeled with SpectrumGold™, EGFR (7p12) labeled with SpectrumGreen™, MYC (8q24) labeled with SpectrumAqua™, and P16 (9p21) labeled with SpectrumRed™.

Cell suspension from each archived cell pellet was manually dropped onto a glass slide using a pipette and hybridized with the final probe set. Slides were coded with a study identification number to ensure blinded evaluation of the specimens. Slides were analyzed with a fluorescence microscope, which has filters for visualization of each fluorescent probe separately to determine the FISH signal pattern of each cell. Starting from one edge of each specimen, signal patterns of 100 consecutive epithelial cells were enumerated and recorded. FISH patterns included disomy (2 signals for each probe), homozygous 9p21 loss (0 copies of 9p21 probe), single locus gain (>2 copies of one locus), single locus gain with concurrent 9p21 loss (>2 copies of one locus with 0 or 1 copy of 9p21), tetrasomy (4 copies per probe), and polysomy (>2 copies of 2 or more probes). After the 100-cell count, the rest of the specimen was subsequently screened, and any abnormal FISH patterns, if present, were recorded. A specimen was considered non-diagnostic if less than 100 cells were present or if the hybridization signals were either not present or obscured.

Each cell was categorized according to its FISH signal pattern. For each specimen, the 100-cell count was used to calculate the percentage of cells with homozygous 9p21 loss. For the other FISH abnormalities (single locus gain, single locus gain with concurrent 9p21 loss, tetrasomy, and polysomy), the absolute number of abnormal cells was tabulated. Patients without carcinoma were considered benign (normal) for statistical analysis. A ROC curve was generated for each FISH abnormality to select a cut-off having the highest sensitivity while maintaining high specificity.

There were 52 males and 45 females in the study, with a mean age of 57 years (range of 20-86 years). Forty-five patients (46%) had primary sclerosing cholangitis (PSC). Fifty-five patients (57%) were diagnosed with carcinoma including cholangiocarcinoma (CCA; n=36), pancreatic adenocarcinoma (n=10), gall bladder adenocarcinoma (n=4), metastatic colon adenocarcinoma (n=2), metastatic breast adenocarcinoma (n=1), plasmacytoma (n=1), and post-transplant lymphoproliferative disorder (n=1). Seven specimens had non-diagnostic FISH results due to lack of cellularity (n=4), obscuring material (n=2), or lacking hybridization signals (n=1).

Based on ROC curve analyses of homozygous 9p21 loss in 100-cell enumerations, absolute number of cells with single locus gain of 1q21, absolute number of cells with single locus gain of 8q24, absolute number of cells with single locus gain of 9p21, absolute number of cells with single locus gain and concurrent 9p21 loss (hemizygous or homozygous), absolute number of cells with tetrasomy, and absolute number of cells with polysomy, optimal cut-off values for positivity utilizing the FISH probe set 1q21, 7p12, 8q24, and 9p21 on pancreatobiliary brushings were selected. The cut-offs are shown in Table 4.

TABLE 4

Cut-off values for positivity utilizing FISH probe set (1q21, 7p12, 8q24, and 9p21) on pancreatobiliary brushings

| FISH Abnormality | Cut-Off Value |
| --- | --- |
| homozygous 9p21 loss | ≥5/100 cells |
| single locus gain (1q21, 8q24, 9p21) | ≥8 cells |
| single locus gain with concurrent 9p21 loss (hemizygous or homozygous) | ≥4 cells |
| Tetrasomy | ≥11 cells |
| Polysomy | ≥4 cells |

Application of the cut-off values for the new probe set resulted in 41 positive specimens. The number of specimens for each respective FISH abnormality detected using the new probe set and the cut-off values is shown in Table 5. Specimens (n=14) that reached the cut-off values for polysomy as well as any other FISH abnormality were categorized as polysomy. Specimens (n=2) that reached the cut-off values for single locus gain with concurrent 9p21 loss as well as single locus gain were categorized as single locus gain with concurrent 9p21 loss.

TABLE 5

FISH abnormalities detected with the new probe set (1q21, 7p12, 8q24, and 9p21) on pancreatobiliary brushings

| FISH Result | N | Number with Carcinoma (%) |
| --- | --- | --- |
| Negative | 50 | 13 (26) |
| homozygous 9p21 loss | 1 | 1 (100) |
| single locus gain (1q21, 8q24, 9p21) | 3 | 2 (67) |
| single locus gain with concurrent 9p21 loss (hemizygous or homozygous) | 4 | 4 (100) |
| Tetrasomy | 1 | 1 (100) |
| Polysomy | 32 | 28 (88) |

A total of 90 specimens had diagnostic FISH results by both probe sets. When considering the UroVysion™ probe set, polysomy was the only FISH abnormality considered positive per standard clinical practice. UroVysion™ was truly positive in 21 specimens, two of which were negative by the new probe set. The new FISH probe set was truly positive in 36 specimens, 18 of which were negative by UroVysion™. Performance characteristics of the new FISH probe set (when utilizing the cut-off values in Table 4) compared to UroVysion™ for the detection of pancreatobiliary malignancy are shown in Table 6. The new probe set was significantly more sensitive than UroVysion™ (73% vs. 41%, respectively). One case was falsely positive by UroVysion™, while five cases were falsely positive by the new probe set.

TABLE 6

Sensitivity and specificity of UroVysion ™ compared to the new probe set for the detection of pancreatobiliary malignancy in brushing specimens

| | N | New Probe Set | UroVysion ™ | P-value (McNemar test) |
| --- | --- | --- | --- | --- |
| Sensitivity | 49 | 36 (73%) | 20 (41%) | <0.001 |
| Specificity | 41 | 36 (88%) | 40 (98%) | 0.046 |

Thus, a new FISH probe set that contains probes directed to 1q21 (MCL1), 7p12 (EGFR), 8q24 (MYC), and 9p21 (P16) was applied to pancreatobiliary brushing specimens for the selection of cut-off values (Table 4). The associated sensitivity for the detection of pancreatobiliary malignancy was significantly higher (P<0.001) with the new probe set compared to the currently employed FISH probe set (i.e., UroVysion™). The new probe set detected 16 additional patients (32%) with cancer compared to UroVysion™. Five patients without malignancy were identified as positive with the new probe set, one of which was also considered positive by UroVysion™. The specificity of the new probe set compared to UroVysion™ was significantly different (P=0.046).

Example 3

This example demonstrates the validation of the cut-offs employed in the analysis of the ERCP brushings with the FISH probes in Example 2.

A separate set of patient brushing specimens was evaluated. The performance of the new probe set was compared to UroVysion™ and routine cytology for the detection of carcinoma.

Per standard practice, ERCP brushings were collected for routine cytology and UroVysion™ FISH. Residual cell pellets from 112 unique and consecutive patients evaluated between 2006 and 2008 were retrospectively identified. The inclusion criteria and the gold standard for malignancy were the same as that utilized in Example 2.

Per standard practice, each specimen was split equally for routine cytology and UroVysion™ FISH in the Mayo Clinic Molecular Cytology Laboratory. For routine cytology, a ThinPrep slide was Pap-stained and evaluated by a cytopathologist as negative, atypical, suspicious, or positive for malignancy. A cell suspension was manually dropped on a slide for hybridization with the UroVysion™ FISH probe set. FISH slides were considered positive if ≥4 polysomic cells were present.

Residual cell pellets were retrospectively utilized to prepare manually dropped slides for hybridization with the pancreatobiliary FISH probe set. Slide preparation, FISH hybridization, and analysis were performed as described in Example 2. Cut-off values from the brushing cut-off study (Table 4) were applied to the cell counts generated from analysis of the brushing validation specimens to generate a pancreatobiliary FISH result for each specimen.

There were 67 males and 45 females in the study, with a mean age of 58 years (range, 23-94 years). Forty-five patients (46%) had PSC. Sixty-five patients (58%) were diagnosed with carcinoma including CCA (n=49), pancreatic adenocarcinoma (n=8), metastatic cancer (n=4), gall bladder adenocarcinoma (n=3), and ampullary adenocarcinoma (n=1). Routine cytology results (Table 7) included 55 (49%) negative, 24 (21%) atypical, 15 (13%) suspicious, and 18 (16%) positive. The proportion of specimens with carcinoma per routine cytology diagnostic category is listed in Table 7.

TABLE 7

Proportion of specimens with carcinoma based on routine cytology result in 112 pancreatobiliary brushings

| Routine Cytology Result | No. with Carcinoma |
| --- | --- |
| Negative (n = 55) | 24 (44%) |
| Atypical (n = 24) | 9 (38%) |
| Suspicious (n = 15) | 14 (93%) |
| Positive (n = 18) | 18 (100%) |

FISH results (Table 8) included 50 (46%) with polysomy; 4 (4%) with tetrasomy; 6 (5%) with single locus gain of 1q21, 8q24, or 9p21; and 52 (46%) negative. The proportion of specimens with carcinoma per FISH diagnostic category is listed in Table 8.

TABLE 8

Proportion of specimens with carcinoma based on FISH abnormalities detected with the pancreatobiliary probe set (1q21, 7p12, 8q24, 9p21) in 112 pancreatobiliary brushings

| Pancreatobiliary FISH Probe Set Result | No. with Carcinoma |
| --- | --- |
| Negative (n = 52) | 12 (23%) |
| Single Locus Gain 1q21, 8q24, or 9p21 (n = 6) | 4 (67%) |
| Single Locus Gain 1q21, 7p12, or 8q24 with concurrent 9p21 loss (n = 0) | NA |
| Tetrasomy (n = 4) | 1 (25%) |
| Polysomy (n = 50) | 48 (96%) |

NA = not applicable

Performance characteristics of the pancreatobiliary FISH probe set (when utilizing the cut-off values in Table 4), UroVysion™, and routine cytology in the validation set of brushings are shown in Table 9. Per standard clinical practice with the UroVysion™ probe set, polysomy was considered positive for statistical calculations for both probe sets. Only positive routine cytology results were considered relevant in clinical practice. Therefore, atypical and suspicious cytology results were considered negative for statistics. The pancreatobiliary probe set was significantly more sensitive than routine cytology (74% vs. 28%, P<0.0001) and UroVysion™ (74% vs. 51%, P=0.0003) with similar specificity. Fourteen additional cases of cancer were detected with three fewer false positives by the pancreatobiliary probe set compared to UroVysion™.

TABLE 9

FISH cut-off validation brushings: Sensitivity and specificity of routine cytology, UroVysion ™, and the pancreatobiliary FISH probe set for the detection of pancreatobiliary malignancy in brushing specimens

| | N | Routine Cytology** | UroVysion* | Pancreatobiliary Probe Set* | Routine Cytology vs. Pancreatobiliary Probe Set (P-value) | UroVysion vs. Pancreatobiliary Probe Set (P-value) |
| --- | --- | --- | --- | --- | --- | --- |
| Sensitivity | 65 | 18 (28%) | 33 (51%) | 48 (74%) | <0.0001 | 0.0003 |
| Specificity | 47 | 47 (100%) | 42 (89%) | 45 (96%) | NS | NS |

*polysomic considered positive
**atypical and suspicious results considered negative
NS = not significant The results of this study indicate that the FISH cut-off values generated for the pancreatobiliary probe set on ERCP brushing specimens are appropriate. Application of these cut-off values to an independent cohort of patients resulted in a significantly higher sensitivity than UroVysion™ or routine cytology with similar specificity. These data not only validate the cut-off values, but also demonstrate clinical utility of the pancreatobiliary FISH probe set.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:

1. A set of detectably labeled probes for detecting pancreatobiliary cancer in a patient, wherein the set of detectably labeled probes consists of a locus-specific probe for MCL1 (myeloid cell leukemia sequence 1), which hybridizes to q21 on human chromosome 1, a locus-specific probe for EGFR (epidermal growth factor receptor), which hybridizes to p12 on human chromosome 7, a locus-specific probe for MYC, which hybridizes to q24 on human chromosome 8, and a locus-specific probe for P16, which hybridizes to p21 on human chromosome 9, and wherein each probe is detectably labeled with a distinct fluorophore.

2. A kit consisting of:
   (a) a set of detectably labeled probes that enables detection of pancreatobiliary cancer in a patient, wherein the set of detectably labeled probes consists of a locus-specific probe for MCL1 (myeloid cell leukemia sequence 1), which hybridizes to q21 on human chromosome 1, a locus-specific probe for EGFR (epidermal growth factor receptor), which hybridizes to p12 on human chromosome 7, a locus-specific probe for MYC, which hybridizes to q24 on human chromosome 8, and a locus-specific probe for P16, which hybridizes to p21 on human chromosome 9,
   (b) instructions for detecting pancreatobiliary cancer in the patient, wherein the instructions comprise determining in a sample of pancreatobiliary cells obtained from the patient the presence of chromosomal abnormalities, and optionally
   (c) one or more items selected from the group consisting of a blocking agent, a label, a labeling agent, a reagent for hybridization, a buffer, and a metaphase spread,
wherein each probe is detectably labeled with a distinct fluorophore, and wherein polysomy is indicative of high-grade dysplasia, pancreatobiliary cancer, or metastatic cancer to the pancreatobiliary tract whereas tetrasomy, P16 loss, single locus gain of MCL1, MYC or P16, or single locus gain of MCL1, EGFR, or MYC with concurrent P16 loss infers increased risk of high-grade dysplasia, pancreatobiliary cancer, or metastatic cancer to the pancreatobiliary tract.

3. A method comprising contacting a sample of pancreatobiliary cells from a patient with the set of detectably labeled probes according to claim 1 and determining the presence of chromosomal abnormalities.

\* \* \* \* \*